(12) United States Patent
Wesner

(10) Patent No.: US 8,535,876 B2
(45) Date of Patent: Sep. 17, 2013

(54) LASER-MICRO-DISSECTION METHOD AND DEVICE FOR LASER-MICRO-DISSECTION

(75) Inventor: Joachim Wesner, Lahnau (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 1251 days.

(21) Appl. No.: 11/917,710

(22) PCT Filed: Jun. 14, 2006

(86) PCT No.: PCT/EP2006/063236
§ 371 (c)(1),
(2), (4) Date: Dec. 14, 2007

(87) PCT Pub. No.: WO2006/134142
PCT Pub. Date: Dec. 21, 2006

(65) Prior Publication Data
US 2008/0194011 A1    Aug. 14, 2008

(30) Foreign Application Priority Data

Jun. 16, 2005    (DE) .................... 10 2005 028 062

(51) Int. Cl.
*C12Q 1/00* (2006.01)
*G01N 1/28* (2006.01)
*G01N 1/44* (2006.01)
*C12M 1/00* (2006.01)
*C12M 3/00* (2006.01)

(52) U.S. Cl.
USPC ...... 435/4; 435/40.52; 435/283.1; 435/286.2; 435/808

(58) Field of Classification Search
USPC ................. 435/40.52, 808, 4, 283.1, 286.2
See application file for complete search history.

(56) References Cited

U.S. PATENT DOCUMENTS

| 6,063,072 | A | * | 5/2000 | Muller ............................ 606/5 |
| 6,773,903 | B2 | | 8/2004 | Bova |
| 6,787,301 | B2 | | 9/2004 | Ganser et al. |

FOREIGN PATENT DOCUMENTS

| DE | 100 43 506 C1 | 12/2001 |
| DE | 103 05 876 A1 | 8/2004 |
| DE | 103 46 458 A1 | 5/2005 |

OTHER PUBLICATIONS

Machine translation of Baeuerle et al. (DE 103 46 458).*
G. Isenberg et al., "Cell surgery by laser micro-dissection: a preparative method", Journal of Microscopy, vol. 107, May 1976, pp. 19-24.

* cited by examiner

*Primary Examiner* — Nathan Bowers
*Assistant Examiner* — Gautam Prakash
(74) *Attorney, Agent, or Firm* — Foley & Lardner LLP

(57) ABSTRACT

A laser-micro-dissection method and a device for laser micro-dissection involves cutting a dissectate from a biological sample, which is applied to a planar carrier, by means of laser pulses along a closed cutting line. The parameters, which determine the laser pulses and the cut lines, are synchronous in relation to the laser pulses and are continually modified along the closed cut line. All elements which are arranged in the optical axis and which determine the parameters of the laser pulse and the cut lines, are controlled by a central calculation unit.

18 Claims, 15 Drawing Sheets

LASER-MICRO-DISSECTION METHOD AND DEVICE FOR LASER-MICRO-DISSECTION

BACKGROUND

The invention relates to a laser microdissection method with the aid of which a dissectate is cut out along a closed cutting line from a biological specimen, which is mounted on a planar carrier, by means of laser pulses of a laser.

Furthermore, the invention relates to a device for laser microdissection that comprises a microscope having at least one objective defining an optical axis. Furthermore, a pulsed laser is provided that emits a laser beam that is directed along the optical axis onto a specimen via the objective and describes a closed cutting line.

In the field of biology and medicine, microdissection denotes a method with which a small piece, a so-called dissectate, is cut out of a generally flat specimen (for example cells, cell cultures or a tissue section) with the aid of a focused laser beam. The biological specimen is mounted for laser cutting on a planar carrier, for example a glass specimen slide or a polymer film. The dissectate is available after the cut for further biological or medical (for example histological) examinations.

Such a method for a laser microdissection is described in the article entitled "Cell surgery by laser microdissection: a preparative method" by G. Isenberg, W. Bilser, W. Meier-Ruge, E. Remy, Journal of Microscopy, vol. 107, May 1976, pages 19-24. A biological specimen is mounted there on the underside of a specimen slide. What is meant by biological specimen is cell cultures that have been attracted on a specimen slide. In order to prevent a permanent adhesion of these cells on the substrate, use is made of silicone-coated specimen slides that effect a reduction in the adhesion between specimen and specimen slide. The specimen slide lies in an erect microscope into which a pulsed He—Ne laser is coupled. The laser beam is focused onto the biological specimen. A specimen field of interest, the dissectate, is cut out along a closed cutting line by juxtaposing cut holes produced by the laser pulses with the aid of the focused laser beam. The cutting is based in this case on the known principle of laser ablation, that is to say the individual laser pulses produce on the cutting line a plasma that "vaporizes" the specimen material. In this case, the last laser pulse separates the dissectate from the surrounding biological specimen and in so doing it also effects the required loosening of the dissectate from the specimen slide. The dissectate then falls down under the action of gravity, and is captured in a collecting vessel and fed to further examinations.

DE 100 43 506 C1 describes a further development of this method. In this case, the specimens to be examined and from which specimen fields of interest are to be cut out are prepared on very thin plastic films. The thickness of these plastic films is of the order of magnitude of 1-2 μm. PET films and PEN films come into question as material. The specimen is loaded into a microscope into which a pulsed laser is coupled. A method for laser microdissection is described in which the cutting line is not completely closed toward the end of the cut, but a narrow and at the same time stable web remains at the end. This prevents the film with the specimen field of interest from being swung out and twisted outside the focal plane. Before the web is severed, the aperture of the laser beam is enlarged by means of a diaphragm without varying the observation aperture of the microscope. The cutting width of the laser beam is enlarged by the enlarged laser aperture. At the same time, the position of the focus of the laser beam is kept without variation at the same position relative to the specimen. The residual web is then severed with the expanded laser aperture with the aid of a last, focused, cutting laser pulse. At the termination of the cut, the specimen falls down under the action of gravity and is collected in a collecting vessel. However, it has emerged overall that it is complicated in terms of equipment and time-consuming to stop the cutting line before the last laser pulse and to switch over the diaphragm for the laser aperture before the cutting line is terminated with the last laser pulse. Again, it proves not to be quite so simple for the user to fix a suitable residual web and to assign a fitting laser aperture, and so the dissectates are sometimes not entirely freely prepared and the cut has to be repeated.

Moreover, it has been observed in the case of both methods that when the equipment setting (optics, laser parameters, focal position etc.) is not varied, dissectates sequentially cut out drift away laterally to a different extent when they fall into the collecting apparatus. This collecting apparatus can be, for example, a specimen tube, usually referred to in the market as a PCR tube. The consequence is then that the dissectates adhere laterally to the inner wall of the PCR tube instead of falling to the bottom of the tube. It is then difficult for them to be inspected, and this constitutes for the user, for example a pathologist, a substantial working step before the further processing of the cutout dissectates.

Consequently, German patent application DE 103 46 458 proposes a method for laser microdissection of a specimen field of interest of a specimen in which the laser pulses of a pulsed laser beam are likewise focused on the specimen, and in the case of which the mass ablated at the last laser pulse completing the cut is adapted to the cutting width of the last cutting laser pulse and optimized so as to maximize the energy transferred from the plasma on to the dissectate.

However, the stopping of the cutting line before the last laser pulse is felt to be time-consuming by the user here too.

U.S. Pat. No. 6,773,903 likewise discloses a method for microdissection in which selected fields of a biological specimen are cut out. The specimen mounted on the specimen slide lies on a stage movable in the x-y coordinate plane. A laser beam is coupled into the microscope and the x-y stage is appropriately moved such that this laser beam describes an appropriately closed cutting line about the specimen field of interest. Consequently, the biological material of interest is separated from the biological specimen. The control of the x-y stage is, however, mechanically complex and not so accurate as if the laser beam were controlled appropriately in the x-y plane in order to separate the biological material from the remainder of the specimen.

It is therefore an object of the invention to specify a method for laser microdissection that permits the dissectate to be cut out in a more comfortable and speedier fashion accompanied by further improved cutting results even in the case of difficult specimen preparation.

This object is achieved by a laser microdissection method described herein.

A further object of the invention is to specify a device for laser microdissection with which the user can obtain the desired dissectates precisely, quickly and reliably. In this case, obtaining the dissectates is independent of the respective specimen preparation.

This object is achieved by a device for laser microdissection described herein.

SUMMARY

In the case of the inventive laser microdissection method, a dissectate is cut out from a biological specimen by means of laser pulses of a laser beam. In this case, the laser beam is guided along a closed cutting line. The specimen itself is mounted on a planar carrier. While the dissectate is being cut out, parameters that determine the laser pulses and the cutting line are continuously varied along the closed cutting line.

The continuous variation of the parameters along the closed cutting line is determined by image processing. The variables for the continuous variation of the parameters along the closed cutting line are obtained from the image processing. These variables are, for example, the specimen thickness, the texture of the specimen, the distribution of the staining inside the specimen, etc.

It is likewise conceivable that the parameters that determine the laser pulses and the closed cutting line are continuously varied only before a closure of the closed cutting line. The parameters remain constant during the rest of the cutting of the specimen.

A slider can be used on a user interface to vary the parameters that determine the continuous variation before the closure of the closed cutting line.

The parameters are determined by means of a central processor, the central processor supplying corresponding control signals to the individual elements of an optical system.

The laser pulses traverse the optical system before they strike the biological specimen, the parameters of the laser pulses being varied with regard to an aperture, an attenuation, a density of the individual laser points on the cutting line and a focal position of the laser pulses.

The aperture and the attenuator are varied simultaneously. The variation of the aperture and of the attenuator is performed synchronously with the laser pulses in order thereby to obtain the highest cutting speed. The variation of the aperture can be carried out by means of a pinhole diaphragm or an iris diaphragm.

The density of the individual laser points inside a cutting line can be adapted with regard to the respective laser power and the local properties of the specimen.

The inventive device for laser microdissection comprises a microscope having at least one objective defining an optical axis. Likewise provided is a pulsed laser that emits a laser beam that is directed along the optical axis onto a specimen via the objective. The laser beam describes a closed cutting line on the specimen in order thereby to separate a selected field of the specimen from the rest of the surrounding biological material. All the elements arranged on the optical axis, which determine the parameters of the laser pulses and the cutting line, are connected to a central processor.

By means of image processing the central processor attains a continuous variation of the parameters along the closed cutting line via a correlated adjustment of the individual elements.

In this case, the central processor can likewise be used such that the central processor continuously varies the parameters that determine the laser pulses and the cutting line only before a closure of the closed cutting line.

The elements that determine the parameters of the laser pulses and the cutting line are an X/Y displacement unit, an aperture unit, an attenuator unit, a focusing unit, a UV laser and a deflecting unit. The central processor in this case supplies appropriate adjusting signals to the respective elements.

Likewise connected to the device for laser microdissection is a monitor on which a user interface is displayed to the user. The user interface constitutes a slider with which the continuous variation of the parameters can be determined before the closure of the closed cutting line. The central processor in this case varies the aperture and the attenuator simultaneously.

Further advantageous refinements of the invention can be gathered in this case from the subclaims.

BRIEF DESCRIPTION OF THE DRAWINGS

The invention is described more accurately below with reference to the schematics, in which.

DETAILED DESCRIPTION

Figure 1:
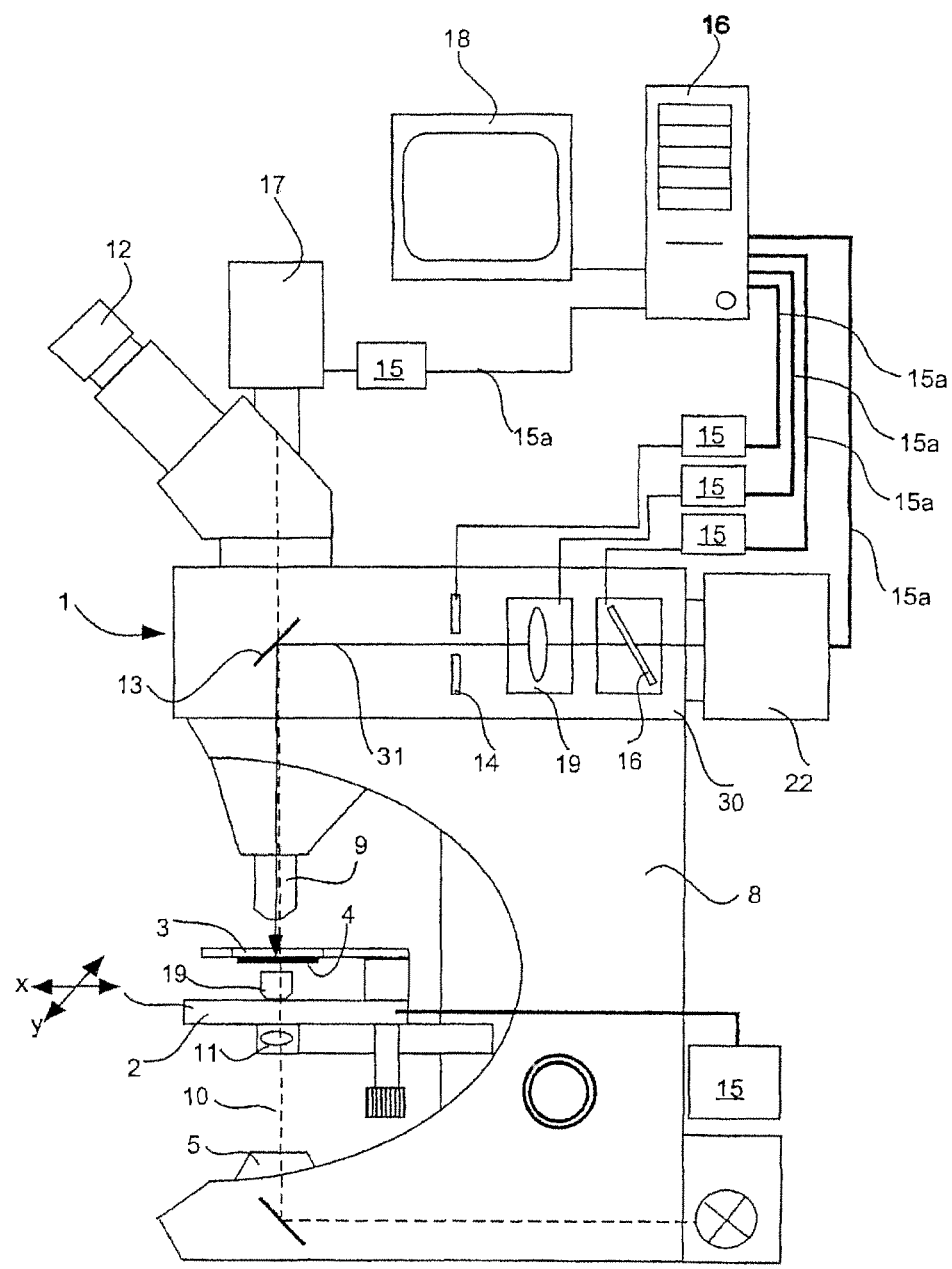
FIG. 1 shows a device for laser cutting with the aid of a stationary laser beam.

Identical elements are denoted in the figures by the same reference numerals.

FIG. 1 illustrates a device for microdissection that operates with the aid of a stationary laser beam and a specimen 4 moved relative thereto. The device comprises a microscope 1 having an x-y stage 2 that can be moved by motor. The x-y stage 2 serves to receive a specimen holder 3 on which a specimen 4 to be examined and/or cut is mounted. Also provided is an illumination system 5 with which the specimen 4 is possible for visual observation by the user via an eyepiece 12. In order to cut the specimen 4, a laser beam 22 is provided that is coupled into the optical axis 10 of the microscope. The laser beam 31 produced by the laser 22 is focused onto the specimen 4 for the purposes of cutting. The x-y stage 2 is connected to a control unit 15 that moves the x-y stage 2 in such a way that the desired cutting line is generated. The appropriate specimen part is then cut out of the specimen by means of the desired cutting line by means of the relative movement between the laser beam 31 and the specimen 4. The microscope illustrated in FIG. 1 is a transmitted-light microscope in the case of which the illumination system 5 is arranged on a microscope stand 8 below the x-y stage 2 and the specimen 4. The microscope 1 comprises at least one objective 9 that is arranged above the x-y stage 2 and the specimen 4. The objective defines an optical axis 10 that is aligned with the optical axis of the illumination system 5. In this described arrangement, the specimen 4 is viewed with the aid of a transmitted-light illumination. The laser cutting could also likewise be executed with the aid of an inverse microscope in the case of which the illumination system 5 is arranged above the x-y stage 2, and that at least one objective is arranged below the x-y stage 2. The light emanating from the illumination system 5 is directed from below by a condenser 11 onto the specimen holder 3, arranged on the x-y stage 2, with the specimen 4. The light penetrating the specimen 4 passes to the objective 9 of the microscope 1. Inside the microscope, the light is fed to the at least one eyepiece 12 via lenses (not illustrated) and mirrors. Likewise connected to the microscope 1 is a camera 17 that records an image section of the specimen 4 as a function of the magnification of the objective. The image data recorded by the camera are passed on to a processor 16 that, for, its part, is connected to a monitor 18 on which an image of the recorded specimen field can be displayed to the user. A control unit 15 is likewise interposed between the camera and the processor. The laser beam 31 emanating from the laser 22 is coupled into the beam path 10 of the microscope via a beam splitter 13, such as, for example, a dichromatic splitter. Before the laser beam 31 is coupled into the beam path of the microscope 1, it traverses an optical system in which a number of elements 14, 16 and 19 are provided. The first element in the optical system is an aperture unit 14 that is connected to a control unit 15, that for its part is connected in turn to the processor 16. The aperture unit 14 can comprise an iris diaphragm or a selection from a number of different pinhole diaphragms. The second element 19 in the optical system 30 is a focusing unit 19 that is for its part likewise connected to a control unit 15 that is likewise connected to the processor 16. The focusing unit 19 serves chiefly for balancing the different focal positions in the ultraviolet of the objectives 9 of the microscope 1, that are chiefly corrected in the visible spectral region. Alternatively the focusing unit 19 can also be used to select a specific focal position or a continuous variation of the focal position of the laser focus during the cutting operation. The third element 16 in the optical system 30 is an attenuator unit 16.

The attenuator unit 16 is likewise connected to a separate control unit 15 that, in turn, is connected to the processor. The laser beam 31 is produced by a UV laser 22 that is introduced into the optical system 30. The UV laser 22 is likewise connected to the processor 16.

The attenuator unit 16 can be varied in angular position, and the attenuation is based on the principle of interference. The aperture unit 14, the focusing unit 19 and the attenuator unit 16 can all be varied in their position and/or size by control signals from the individual control units 15. The variation is performed in this case by a motor. The aperture unit 14, the focusing unit 19 or the attenuator unit 16 is connected to the individual control unit 15 that, on its part, is connected to the processor 16 via an individual feedback line 15*a*. The aperture unit 14, the focusing unit 19 and the attenuator unit 16 can in this case be adjusted independently of one another. The independent adjustment of the aperture unit 14 and the attenuator unit 16 yields in combination a maximum dynamic range (variation width of the laser power in the specimen), and the variables such as depth of field, resolution and power density can be influenced in a targeted fashion independently thereof. The specimen 4 is cut with the aid of individual laser pulses using the laser beam 31 coupled into the optical system 30, which is reflected into the beam path 10 of the microscope 1 via a beam splitter. However, an optimum cutting result for the purpose of the invention requires the synchronization of the laser pulses with the variations of all of the aperture unit 14, the attenuator unit 16 and the focusing unit 19, there also being a need to take account of the movements of the x-y stage 2.

Figure 2:
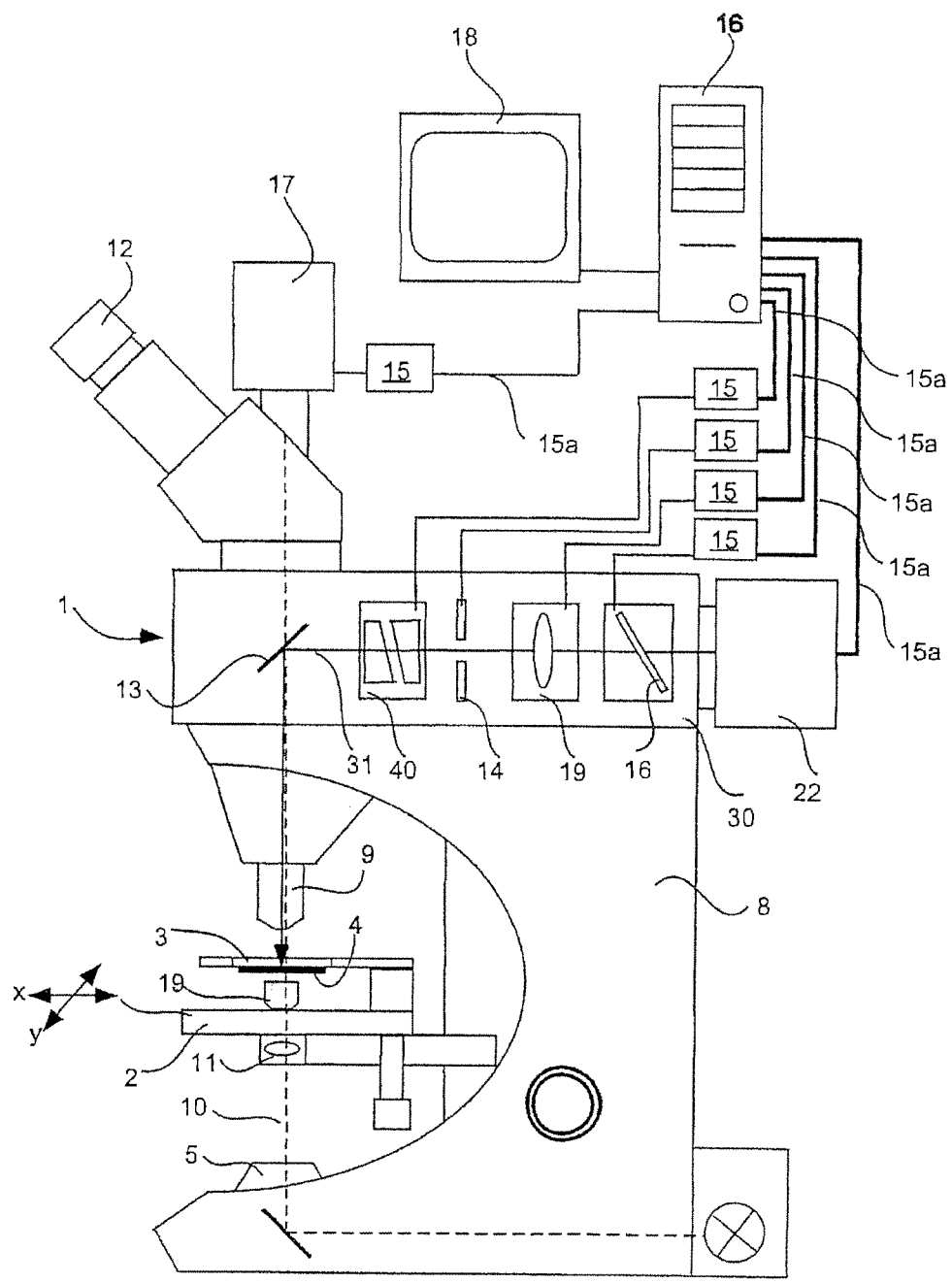
FIG. 2 shows a device for laser cutting with the aid of a movable laser beam.

FIG. 2 shows a device for laser microdissection in the case of which the x-y stage is stationary and the laser beam is deflected in the appropriate way by a deflecting unit 40, that is likewise arranged in the optical system 30, in order to cut out from the specimen 4 a dissectate of any desired shape. In this arrangement the x-y stage 2 cannot be moved during the cutting operation. Proceeding in the direction of the laser beam emanating from the laser 22, the arrangement in the optical system 30 is: firstly the attenuator unit 16, then the focusing unit 19, then the aperture unit 14 and, finally, the deflecting unit 40. The deflecting unit 40 is connected to an individual control unit 15 that, for its part, is connected to the processor 16 via a feedback line 15*a*. The deflecting unit 40 consists of a pair of wedge plates that can be displaced in a suitable way by the control unit 15 in conjunction with the processor 16 so that the laser beam describes on the specimen the desired shape that the cutout dissectate is finally intended to have. As already mentioned in the description relating to FIG. 1, all the elements of the optical system 30 are each connected to individual control units 15 that are connected to the processor 16 via a feedback line 15*a*.

Figure 3:
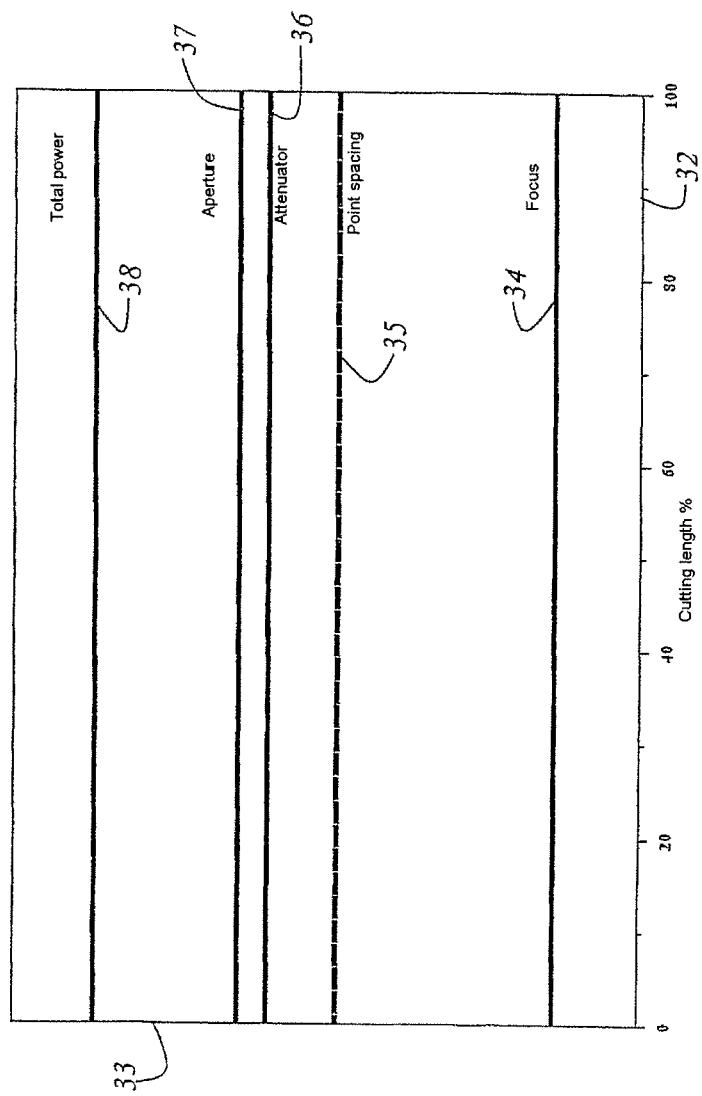
FIG. 3 shows the parameter composition in accordance with the prior art in the case of which the parameters remain constant up to the end of the cutting line.

FIG. 3 shows the set of parameters as used in the case of a cutting method for dissectates in accordance with the prior art. The cutting length in percent is plotted on the abscissa. In this case, 0 percent signifies the beginning of the cut and 100 percent the end of the cut. The individual parameter values are plotted on the ordinate 33 in arbitrary units as a function of the cutting length. All the parameters such as, for example, focus 34, point spacing 35, attenuator 36 and aperture 37 are constant over the entire cutting length. The total power 38 that results from the interaction of attenuator 36 and aperture 37 is therefore likewise constant over the entire cutting length.

Figure 4:
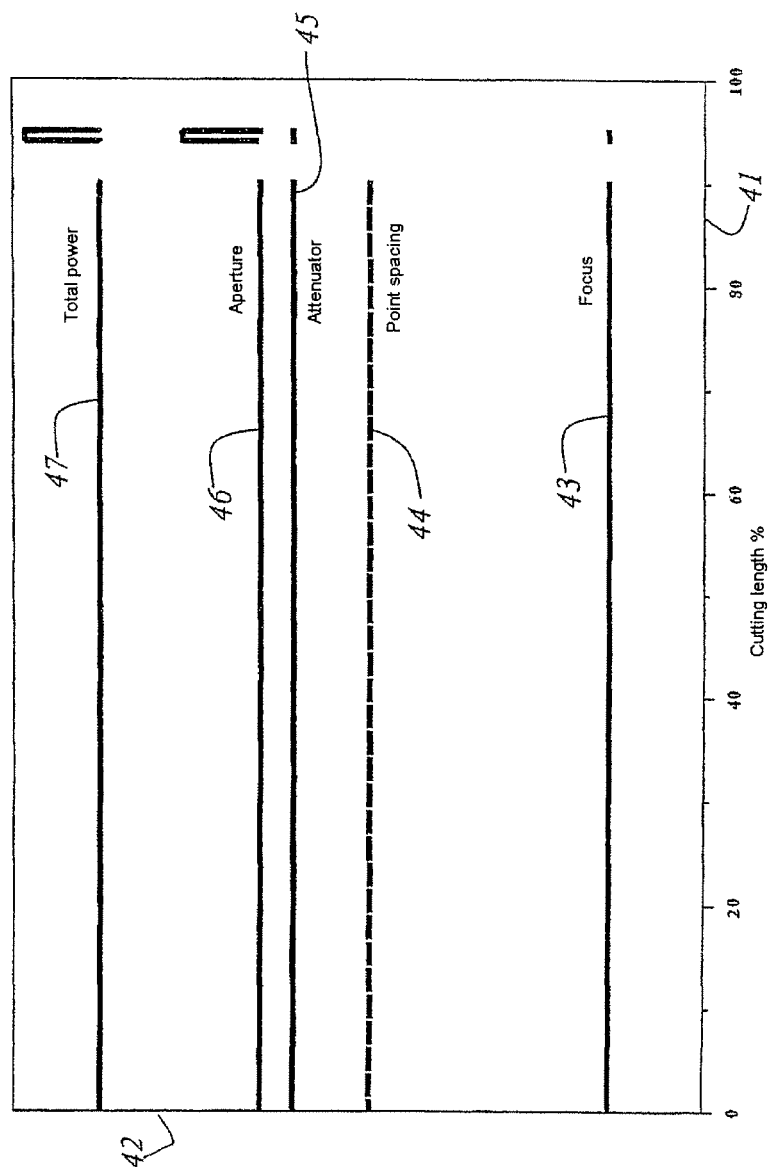
FIG. 4 shows a parameter composition in accordance with the prior art in the case of which the parameters are varied suddenly before the end of the complete cutting out of a specimen.

FIG. 4 likewise describes the combination of parameters during a cutting process of a dissectate in accordance with the prior art. Cutting length is likewise plotted in percent on the abscissa 41, and the value of the parameters is illustrated in arbitrary units on the ordinate 42. The focus 43, the point spacing 44, the attenuator 45 and the aperture 46 are constant over virtually the entire cutting length. As already described in FIG. 3, the parameters of the attenuator 45 and the parameters of the aperture 46 yield a total power 47 that is therefore likewise constant up to shortly before the end of the cutting line. Shortly before the end of the cutting length or cutting line, the system inserts a short pause in which the parameter of the aperture 46 is varied. The aperture is therefore enlarged before the end of the cutting line. Consequently, there is thus also a change in the total power that therefore also becomes larger owing to the large aperture. The other parameters such as, for example, attenuator 45 and focus 43 remain constant in this case.

Figure 5:
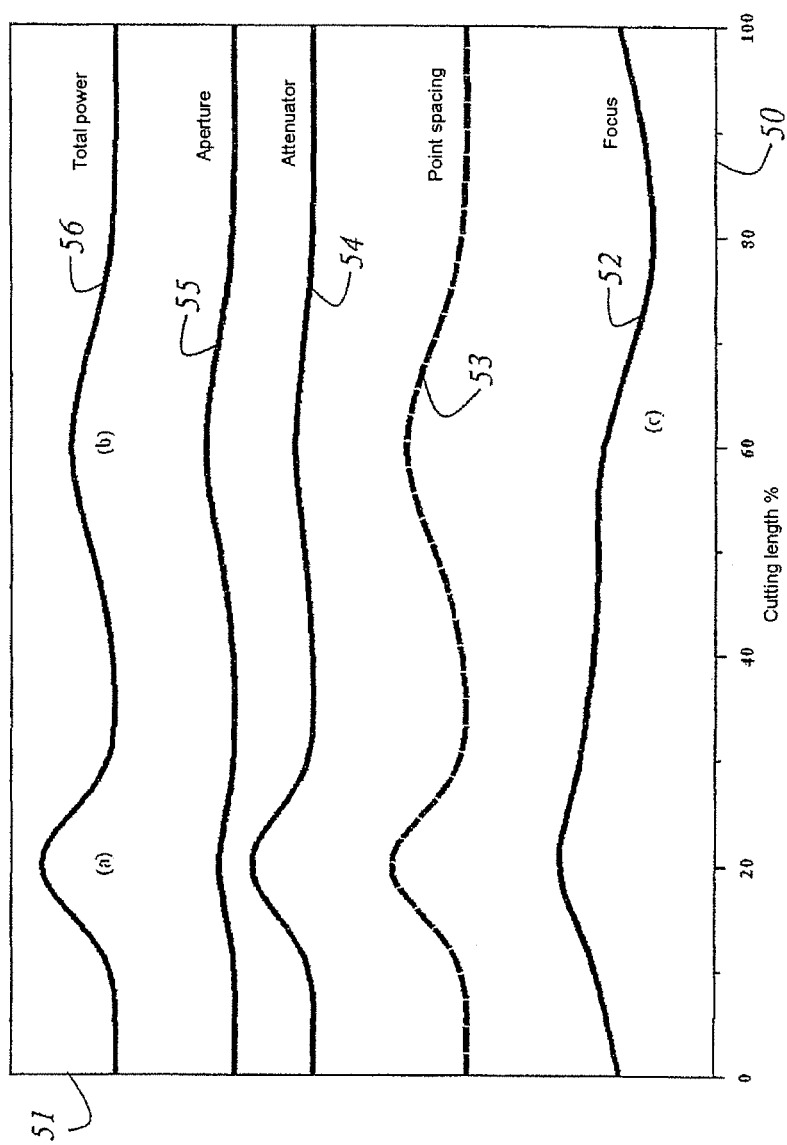
FIG. 5 shows a continuous variation of the parameters along a closed cutting line.

FIG. 5 shows a set of parameters that vary continuously over the entire cutting length. The cutting length is plotted in percent on the abscissa 50, and the continuously varying values of the individual parameters are plotted on the ordinate 51. As may be seen from FIG. 5, the parameters of the focus 52, the point spacing 53, the attenuator 54, the aperture 55 and therefore also the total power 56 vary over the entire cutting length. A variation of the focal position is required in order to balance an oblique position of the specimen, or in order to adapt the focus to different thicknesses of the specimen. Likewise, with the aid of the changing focus it is possible to select a specific z-position or a continuous variation of the z-position of the laser focus during the cutting operation or the production of a cutting line. The cutting line is produced by a juxtaposition of individual laser pulses. It is important in this case that the points touch one another in order thereby to produce a cutting line that separates the dissectate from the rest of the specimen 4. As illustrated in FIG. 5, it is likewise possible to this end to vary the point spacing of the individual laser pulses inside the cutting line. A variation in point spacing signifies the diameter of the individual laser pulse can change during the production of the cutting line. The interaction of the aperture 55 and the attenuator 54 likewise results in a continuously changing total power 56 that is input onto the specimen 4 by the laser pulse. In the case described in FIG. 5, the variables of total power 56, aperture 55, attenuator 54, point spacing 53, as well as the focal position 52 are varied continuously and synchronously with the laser pulses in order to achieve a detachment that is as reliable as possible in conjunction with an optimized cutting speed. Estimated values for these parameters can be determined, for example, by evaluating the optical density in the entire spectral region or in specific spectral regions or color channels, and by "calibrating" the method to the specimen material, that is to say by cutting trials in a part of the specimen not otherwise used. In this case, there is the additional freedom of achieving the same total laser powers from different settings of attenuator and aperture diaphragm, and thus, depending on the section of the cutting line, of selectively, for example, optimizing at (a) or (b) either the depth of field (small aperture) or the power density at the focus (large aperture). A possible curvature and a general inclination of the preparation relative to the optical axis can also be determined (c) via evaluation of the contrast of the microscope image at various focal positions, and can be varied within the scope of the proposed invention simultaneously with the laser pulses and thus without reducing the cutting speed. Estimated values for the cutting properties of the specimen material along the prescribed cutting curves l and $l_i$ are then optionally determined for example by evaluating the optical density d in the entire spectral range or in specific spectral ranges or color channels, or else with the aid of other methods. A profile of the cutting parameters such as total laser power P (see below), aperture A, attenuator K, point density D and, if appropriate, also focal position z along l is determined and stored for the subsequent cutting process on the basis of the optical density d thus estimated, together with user data relating to the type of the specimen material or carrier material x. A few prescribed single parameter functions (P, D, z)=$f_x$(d) or else (A, K, D, z)=$f_x$(d) are also conceivable here for the purpose of simplifying the operation. Alternatively, it is also possible to determine the best cutting parameters by "calibrating" the method to the specimen material, that is to say by means of cutting trials in a part of the specimen 4 not otherwise used.

A possible curvature and a general inclination of the preparation or specimen 4 to the optical axis 10 can also be determined by evaluating the contrast of the microscope image at various focal positions and be varied in the scope of the proposed invention in a fashion simultaneous to the laser pulses and thus without reducing the cutting speed.

Figure 6:
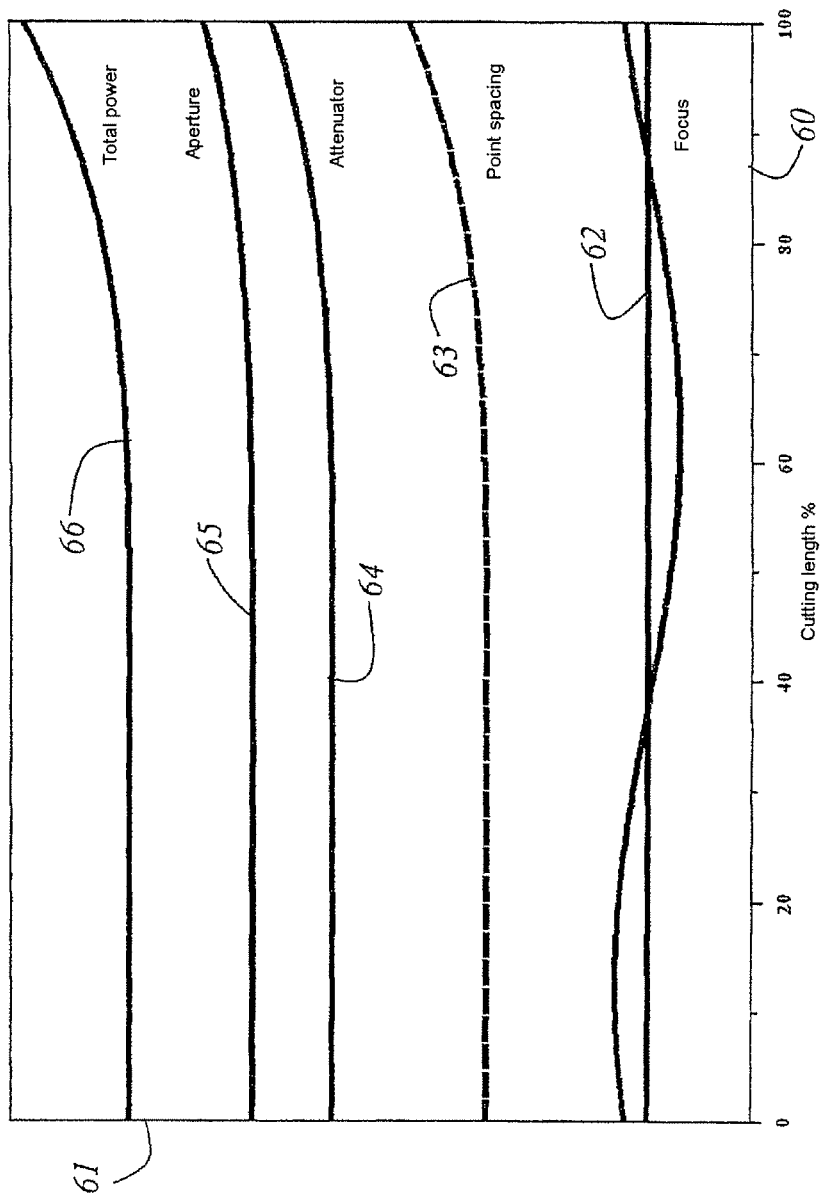
FIG. 6 shows a continuous variation of the parameters before the end of the cutting line.

FIG. 6 describes the situation in which some parameters are changed continuously shortly before the end of the cutting line. The cutting length is plotted in percent on the abscissa 60, and the values of the individual parameters are illustrated in arbitrary units on the ordinate 61. The changing parameters are the focus 62, the point spacing 63, the attenuator 64, the aperture 65 and the total power 66. In this case, the focus 62 can remain constant over the entire cutting line or change continuously over the entire cutting line. Starting from approximately 60 percent of the terminated cutting line, there is a continuous increase in the values of remaining parameters such as point spacing 63, attenuator 64, aperture 65 and, consequently, the total power 66. The previously mentioned values of the parameters are constant up to 60 percent of the cutting line. As a result, a reliable separation of the dissectate from the remainder of the specimen material or the carrier is achieved by a continuous increase in the total power acting on the specimen 4 before the end of the cutting line. An explicit determination of the cutting parameters along the cutting line is dispensed with in the case of the parameter setting shown in FIG. 6. The aim is as reliable as possible detachment of the dissectate in conjunction with the high "overall" cutting speed. No part of the cutting curve is omitted, but laser power (or aperture and attenuator) and point spacing are continuously increased in the end region of the cutting curve in order to minimize premature lowering or, as caused by stresses, setting up of the dissectate from the focal position. These variations are described by classes x of single-parameter functions that take the profile of laser power and point spacing along the cutting line. The selection of x can be performed on the basis of typical (known or previously determined) material properties, or else by a type of "calibration". Alternatively, or else in addition, it has proved to be helpful to the user to influence the selection of the correct function class x via an additional setting variable that describes how critical the respective material is with reference to the interfering effects such as setting up, lowering, tilting, or sliding up and bonding, and that then, for example, prescribes the variations of the total laser power (or of the aperture and the attenuator) and of the associated point density toward the end of the cutting line. The user can thus distinguish in as simple a way as possible between uncritical specimen materials on the one hand, and specimen materials that are difficult to separate on the other hand, and adapt the cutting process correspondingly.

In the simplified case of FIG. 6, no optical density d is determined along the cutting line l and used, but an optimized parameter profile (P, D)=$g_x$(l) or else (A, K, D, z)=$g_x$(l) is determined, $g_x$ again being classes of single-parameter functions that describe the profile of the parameters along the cutting line l, particularly toward the end, in order, as already discussed further above, to achieve both cuts as thin as possible over as large as possible a part of the cutting line l, and as reliable as possible a detachment in the critical end region of l. Selection of x can be performed on the basis of typical (known or previously determined) material properties, or again by means of a type of calibration, as already discussed in the description relating to FIG. 5. Alternatively, or else in addition, it has proved to be helpful to the user to influence the selection of the correct function $g_x$ via an additional setting variable that describes how critical the respective material is with reference to the abovementioned interfering effects such as tilting, sliding up, bonding or bending up, and that then prescribes, for example, the variations of the total laser power P (or A and K) and the associated point density D toward the end of the cutting line. The user can thus distinguish in as simple a way as possible between uncritical specimen materials on the one hand, and specimen materials that are difficult to separate on the other hand, and optimize the cutting process correspondingly.

It is also optionally possible in the cutting method described in FIG. 6 to use contrast evaluation of the microscope image in various focal positions to determine a possible curvature and a general inclination of the preparation relative to the optical axis, and simultaneously to correct the laser pulses without reducing the cutting speed.

Figure 7:
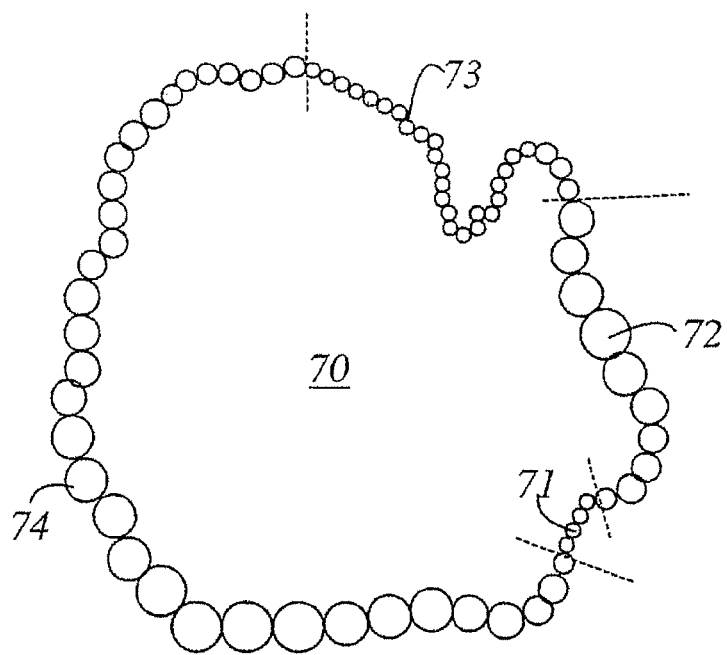
FIG. 7 shows a schematic of a cutting line over the course of which the parameters are varied continuously in the course of the entire cutting line.

FIG. 7 shows a cutting line 70 inside which a number of regions are provided in which the combination of the parameters of the laser pulses on the specimen 4 change. In the present embodiment, the cutting line 70 is subdivided into four regions 71, 72, 73 and 74. Thus, for example, cutting is conducted with constant parameters in the region 71 and in the region 73. In region 72 and in region 74, the parameters for producing the cutting line vary continuously. Either the user employs a mouse (not illustrated) to mark the desired cutting line l directly in the image of the specimen 4 on the monitor 18 or, if appropriate, he roughly prescribes just a search region, and an image detector determines in a fully automatic fashion one or more/all cutting lines $l_i$ in the prescribed region of the specimen 4.

Figure 8:
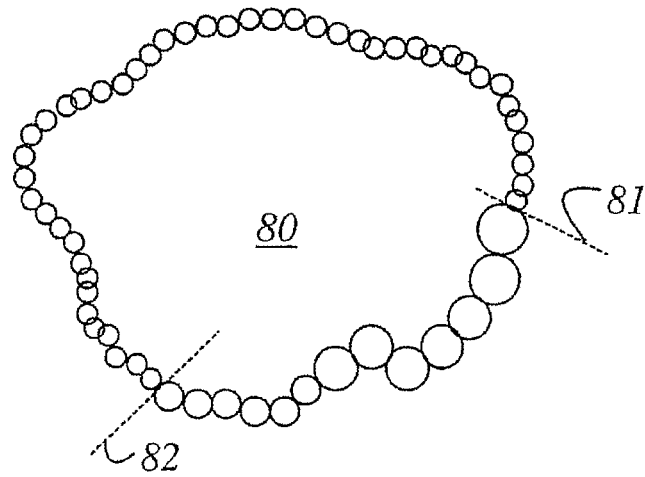
FIG. 8 shows a schematic of the cutting line in the case of which the parameters are not varied before the end of a cutting line.

FIG. 8 shows a further embodiment for producing a cutting line 80. The cutting line has a start that is denoted by 81 in FIG. 8. The start of the cutting line 81 coincides with the end of the cutting line 83. Proceeding from the start 81 of the cutting line, cutting is performed with constant parameters up to a position 82 on the cutting line. The constant parameters are applied in the cutting line between the start 81 and a position 82 in the cutting line. The parameters are then continuously varied or raised between the position 82 and the start or end 81 respectively of the cutting line. Thus, after approximately 60 percent of a completed cutting line, at the earliest, a start is made on continuously varying the cutting parameters up to the end of the cutting line. During the cutting process, the mean width of the cutting line is a few μm.

Figure 9:
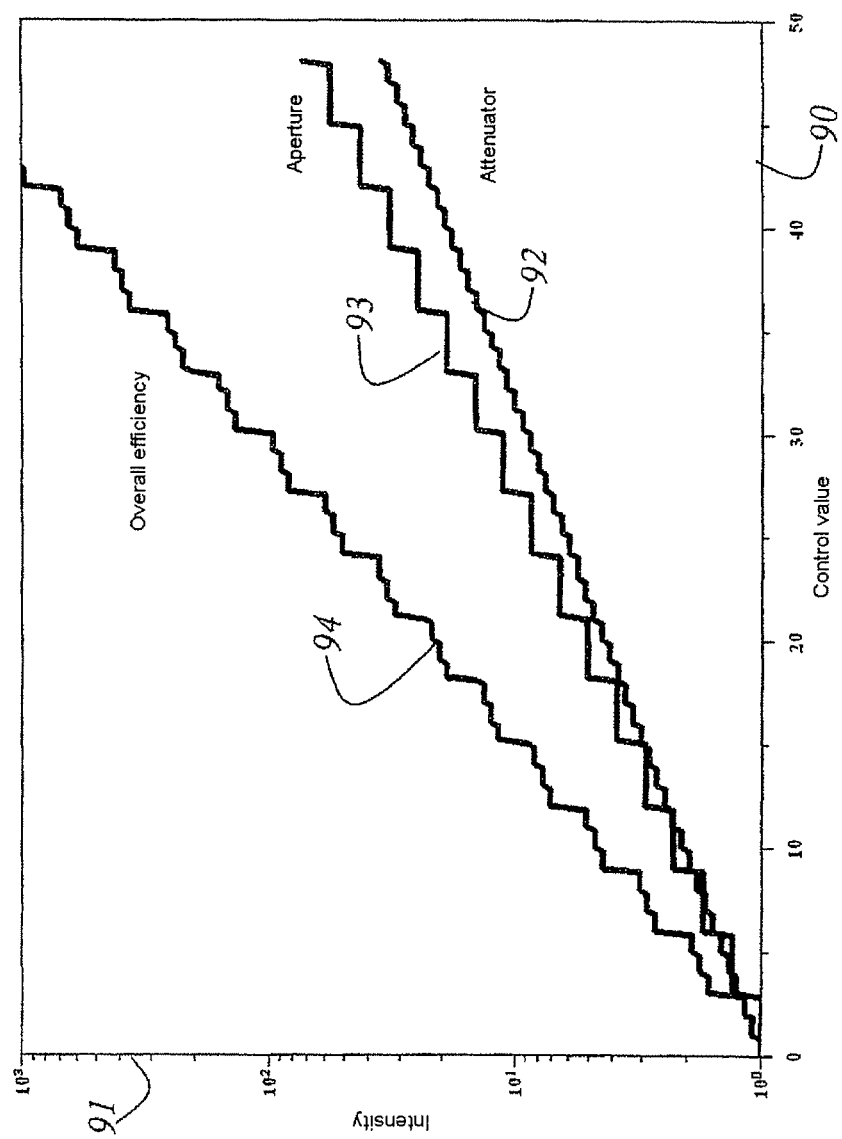
FIG. 9 shows the overall efficiency of the variation of the aperture A and of the attenuator K.

FIG. 9 shows the overall efficiency in the case of simultaneous variation of the aperture and the attenuator. The control value is plotted in arbitrary units on the abscissa 90. The intensity is illustrated in logarithmic units on ordinate 91. Simultaneous variation of aperture and attenuator is required in order to achieve as large a dynamic range as possible. The combined driving of the attenuator and aperture raises the resolution in the case of the power setting. The diaphragm steps are usually only coarsely logarithmically graduated for the aperture. One diaphragm step corresponds to a variation in intensity of >30 percent. The attenuator can, in contrast, be set with a resolution of 7 percent and better (smaller microsteps are possible). A high dynamics (total dynamics of approximately 1:2000) can be achieved by the combined simultaneous driving of aperture and attenuator in conjunction with a resolution of better than 7 percent (100 steps at 0.928). The variation 92 of the attenuator is illustrated with discrete steps in FIG. 9. The variation 93 of the aperture is likewise illustrated in discrete steps in FIG. 9, the steps being larger in the case of the aperture setting than in the case of the setting of the attenuator, as already mentioned above. The overall efficiency of the intensity resulting from the combined driving of the aperture and the attenuator is illustrated in the curve 94. It follows that the curve 94 shows periodic jumps in the rise of intensity in the overall efficiency. During a cutting operation, both the aperture A and attenuator K of the laser beam 31 are varied arbitrarily. However, not all combinations of A and K are in practice independent or sensible for a specific application. In principle, there are a number of combinations of A and K that all lead to the same total power input P into the specimen, and by analogy with photography, many combinations of diaphragm B and exposure time t lead to the same exposure of the film. If A denotes the logarithm of the aperture diameter, and K the logarithm of the transmission of the attenuator, it holds in simplified fashion that P=A+K (with P also in logarithmic units), it thereby being clear that (infinitely) many values of A and K can lead to the same sum P. However, it also holds true here by analogy with photography that the end result can by all means be different even when the mean power import P (the mean exposure in the photograph) is the same. In photography, these properties are taken into account by so-called "program automatics", that is to say the values of B and t are varied over the useful range of the exposure in a specific scheme and, depending on application, the respective scheme is changed or adapted, for example, concerning whether maximum depth of field or whether minimum movement of field is desired. The idea of a "program automatic", that is to say a scheme according to which A and K are varied together, can now be used together with the method described here and the associated device for an improvement of power control in laser microdissection.

The dynamics ranges that can be attained alone with the aid of aperture stop and attenuator are restricted in practice to values of approximately 70:1 or 30:1 in a particular case. However, an optimum cutting quality typically requires the variation of the overall efficiency over a relatively large range. Very large power changes can also be implemented without loss of speed through simultaneously varying the aperture stop and attenuator synchronously with the laser pulses, because the adjustment path of the individual components is less than when the change would have to be implemented solely with the aperture stop and the attenuator alone, and a dynamics range of=2000:1 overall is achieved after all.

In the simplest case (see FIG. 9), aperture and attenuator are varied monotonically over the prescribed range of a control value in order to implement this large dynamic scope. However, in some circumstances this gives rise to unequally large power steps (as already mentioned above). The finer graduation of the attenuator in the example therefore cannot be utilized against the coarsely graduated aperture.

Figure 10:
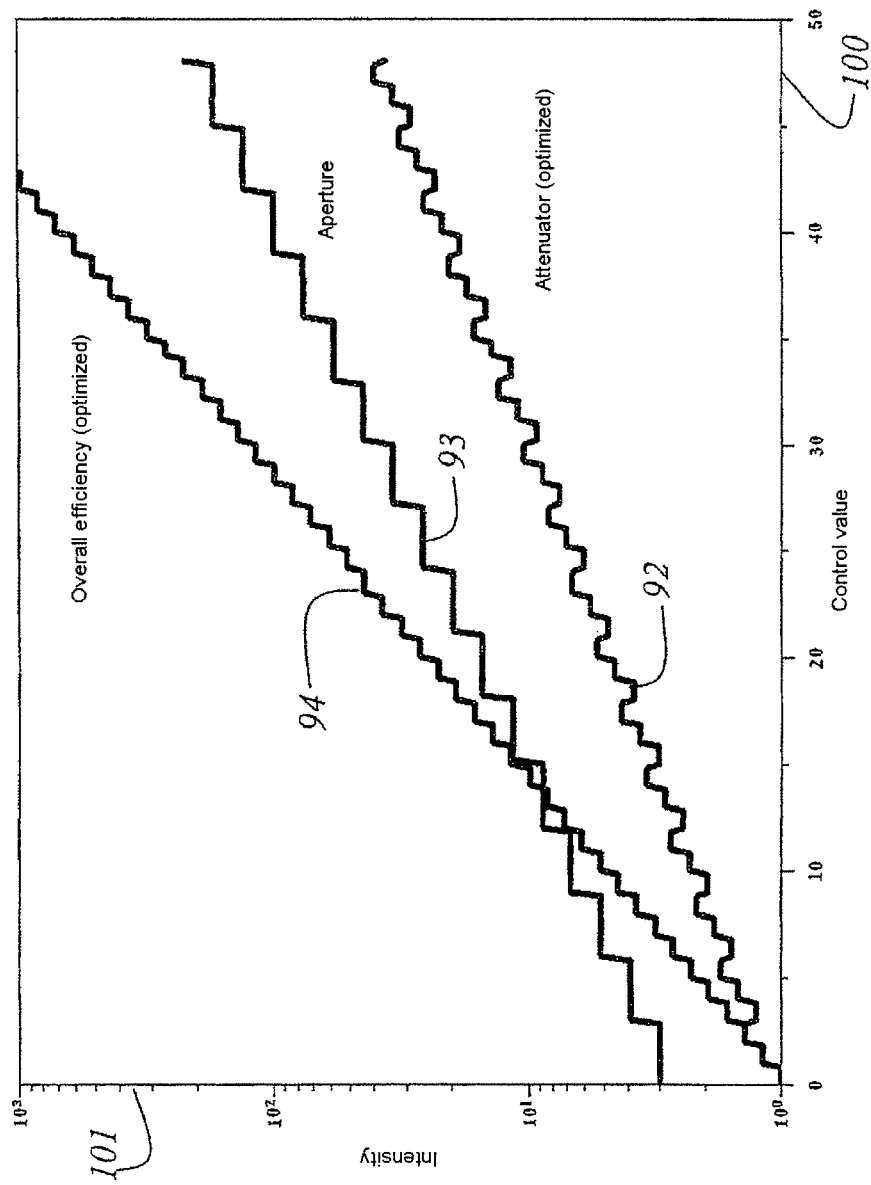
FIG. 10 shows an optimized overall efficiency from the variation of the aperture A and of the attenuator K.

FIG. 10 likewise shows a combination of the overall efficiency of attenuator and aperture. Here, the control value is plotted in arbitrary units on the abscissa 100. The intensity is, in turn, plotted in logarithmic units on the ordinate 101. The curve 92 shows the change in the attenuator. In this case, the attenuator is not continuously changed in a rising fashion in discrete steps. Consequently, the attenuator is varied such that firstly the intensity rises in two steps and drops again in a third step. This scheme is continued for the entire adjustment of the attenuator. As already shown in FIG. 9, the aperture is varied in discrete steps. The overall efficiency resulting from the combination of a varying aperture and a varying attenuator is illustrated in curve 94. It is clearly to be seen that the intensity rises continuously in a stepwise fashion, each of the steps being equally large. It is therefore possible to speak of a quasi continuous rise in the overall efficiency. In addition, the suitable combination of the adjustment of attenuator and aperture gives rise to an overall efficiency that can be adjusted in substantially finer steps. A monotonic, exponential variation of the overall efficiency over the full range=2000:1 can be implemented by maintaining the finer graduation of the attenuator by optimized driving of the attenuator that compensates the errors arising here in the simple case (FIG. 9).

Figure 11:
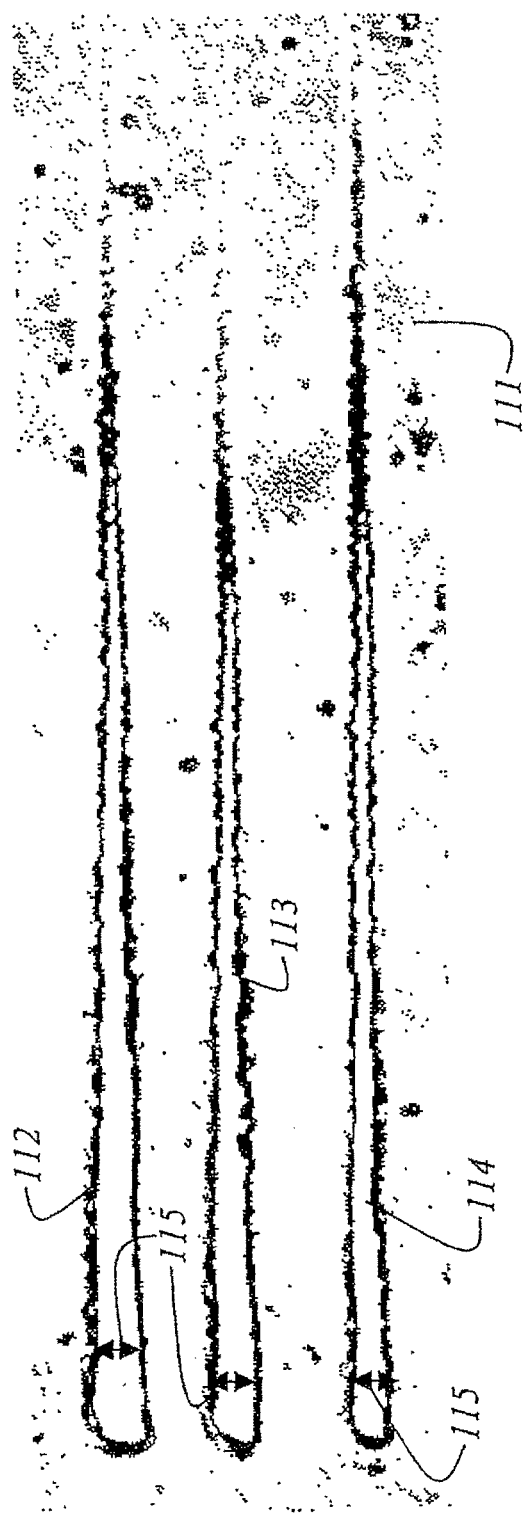
FIG. 11 shows cutting lines in the case of which the aperture diaphragm and the attenuator have been adjusted in common.

FIG. 11 shows the resulting cutting lines 112, 113 and 114, for which the aperture stop and the attenuator have been adjusted in common using the method described in FIG. 10. Each of the cutting lines 112, 113 and 114 is cut in this case with the aid of a different set of parameters from aperture stop and attenuator. All the cutting lines 112, 113 and 114 exhibit a continuous increase in the cutting width 115. Each of the cutting lines 112, 113 and 114 exhibit no jumps in the cutting width 115 because of the adjustment of the aperture stop and of the attenuator according to the method described in FIG. 10. The cutting width at the end of the cutting lines 112, 113 or 114 is approximately 10 μm to 50 μm. Owing to the possibility of fine correction of the power values, even the use of a pinhole diaphragm instead of an iris diaphragm has proved to be definitely advantageous. An iris diaphragm has the advantage in principle that the variation of the aperture values takes place continuously, and so there is no "risk" of a laser pulse striking the space between the prescribed apertures of a pinhole diaphragm during the adjustment, and thus being blocked. By contrast, the aperture values of the pinhole diaphragm are more accurately defined, and a pinhole diaphragm can be of smaller and lighter design such that the adjustment requires only a few ms and can therefore be performed completely in the waiting time between the laser pulses.

Figure 12:
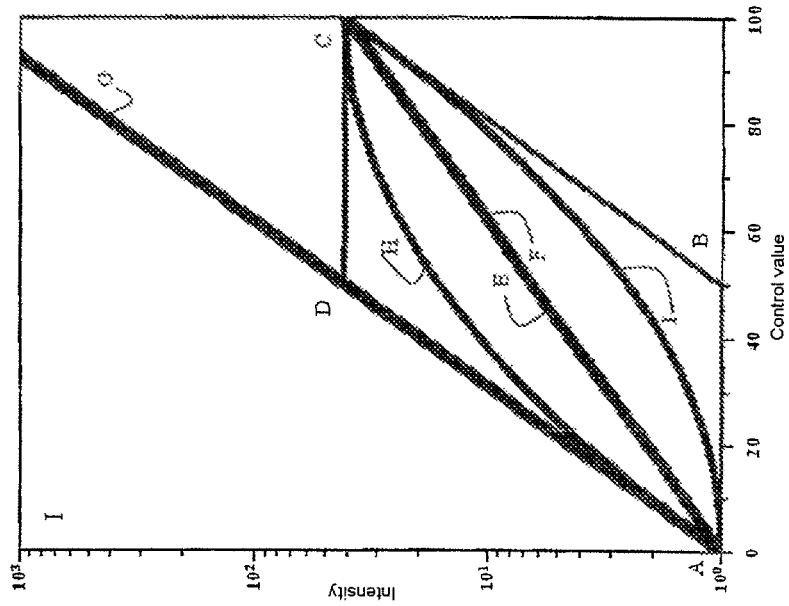
FIG. 12 shows, by way of example, the restrictions of the possible combinations of an attenuator with a dynamic range of 40:1 and an aperture diaphragm of the same dynamic range.

FIG. 12 illustrates for example the restrictions on the possible combinations of an attenuator with dynamic range of 40:1 with an aperture stop of the same dynamic range. In this case, attenuator and aperture stop are driven simultaneously such that over a control value of 0-100 there is a strong exponential variation of the total power of $40^2:1$, that is to say 1600:1, according to the cumulative curve G.

In the simplest and mostly universal case, which is also implemented in FIGS. 9 and 10, both attenuator and aperture stop are varied in the same way in accordance with the curves of constant gradient E and F over the entire range of the control value. It follows that no special preference is accorded to a specific setting value.

However, it can also be rational, for example, to maintain aperture values as low as possible over a range of the control value that is as large as possible, in order to ensure a depth of field as large as possible and/or also to ensure for the cutting optics aberrations to be as slight as possible. Conversely, it can also be rational to prefer an aperture as large as possible, in order to ensure for special substrates in spatial (lateral and axial) resolution as high as possible, and at the same time to ensure as high a power density as possible at the focus (there is a disproportionate rise in the power density due to the fact that the extent of the focal spot decreases with increasing aperture!). These cases correspond to pairings of the control curves such as, for example, H and I, where in the first case l stands for the aperture and H for the attenuator, and vice versa in the second case.

It is found in the general case that for the purpose of driving within the scope of the prescribed object all pairs of curves (and only these!) are possible that run completely in the parallelogram A B C D from A to D and lie in pairwise fashion symmetrically in relation to the line A to D (or, in a fashion equivalent thereto: their sum yields the prescribed value G for a specific control value).

Figure 13:
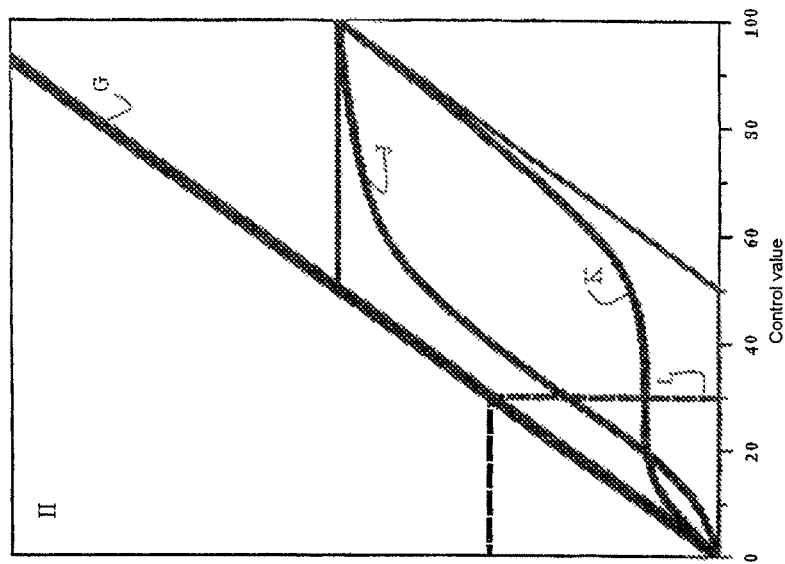
FIG. 13 shows, by way of example, control curves for attenuator and aperture that are in no way restricted just to profiles with monotonic variation of the curvature.

The control curves for attenuator and aperture are illustrated in FIG. 13 in a fashion certainly not restricted only to profiles having monotonic variation of the curvature, but reversal points and regions of (approximately) constant value are also possible. Thus, for example, it can be required to ensure as constant an aperture as possible in accordance with the profile K over as large a range as possible about the control value of, for example, 30 (L). According to the above considerations, it is then possible to directly derive the assigned control curve J for the attenuator from the symmetry in relation to A-D or from the sum condition for G.

The combined driving of aperture stop A and attenuator K, particularly when use is made of the error correction according to FIG. 10, requires a high accuracy of the attenuator values K that are set. Unfortunately, the attenuators used typically approximately exhibit as a function of tilt angle alpha a displaced cos-shaped characteristic $K=f0 \times \cos(f1+f2 \times alpha)+1+f3$ (f0 to f3 are individual parameters) with a maximum and a minimum, and not the desired monotonic exponential form $K=g0 \times \exp(-g1 \times alpha)$.

Figure 14:
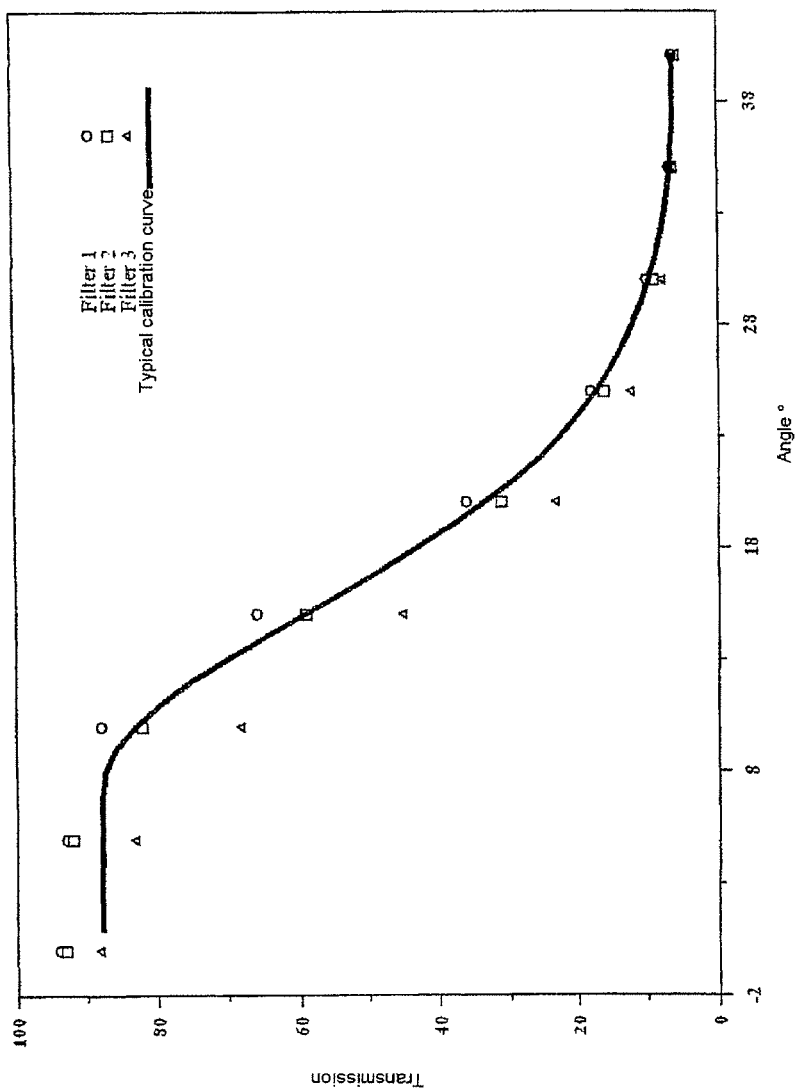
FIG. 14 shows a typical calibration curve as a function of the angular position of the attenuator.
Figure 15:
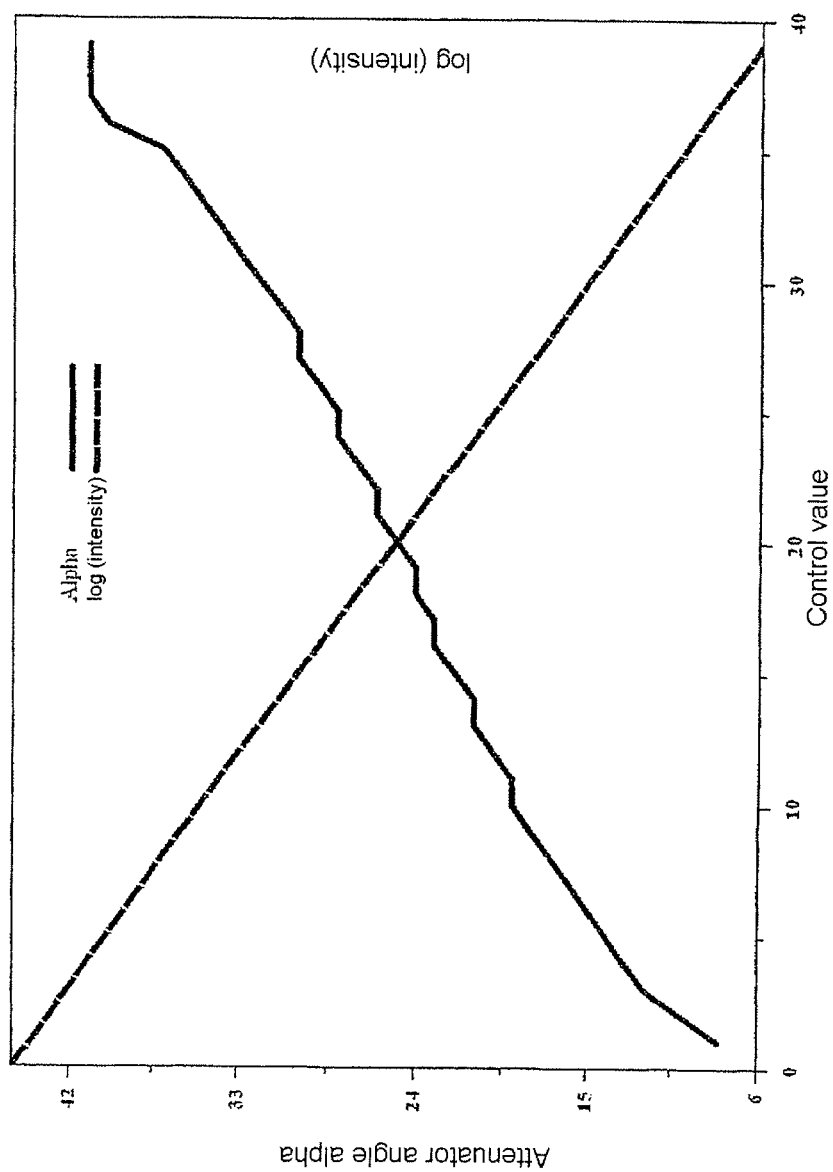
FIG. 15 shows a linearization of the characteristic of the attenuator from a prescribed control value.

Consequently, in order to ensure accuracy for the purpose of the invention fid parameters (four or more) of an individual attenuator or, in the case of sufficiently small dispersion, the mean parameters of a production batch of attenuators are determined (see FIG. 14), and are filed in the memory area of the laser head. By inverting the fid function, it is then possible to determine the associated tilt angle from a prescribed control value, and thus to "linearize" the characteristic of the attenuator (see FIG. 15). It can be required, for example, in a particular case that three levels of the control value correspond with a factor of 1.25 (exponential characteristic). This results in an exponential characteristic of intensity of log 10(Intensity)∝−0.0323×control value.

In order to optimize the cutting speed, the calculations and movements are performed in a time "staggered" fashion, that is to say while the individual components (aperture unit 14, attenuator unit 16, focusing unit 19, and deflecting unit 40 or x-y stage 2) are seeking a new position, or the expiry of the prescribed period for the desired laser frequency is being awaited, time-consuming calculations are already being carried out for the position respectively following thereupon. Once the feedback is then to hand that all the components have reached their desired position AND the prescribed waiting time for the laser pulse has expired, the laser trigger is released and positioning commands are transmitted at once for the following shooting position.

Figure 16:
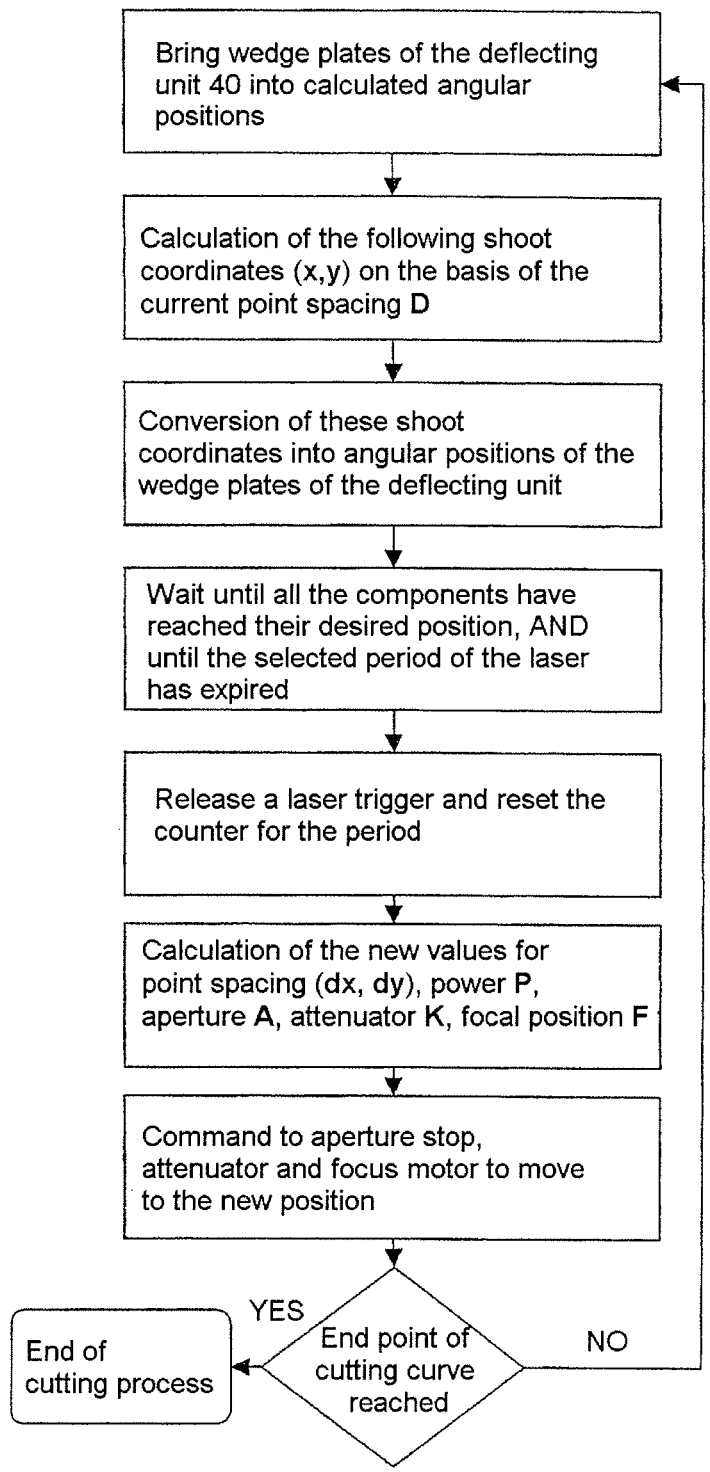
FIG. 16 shows, by way of example, a schematic of a program loop for generating a cutting line.

By way of example, FIG. 16 is a schematic of a program loop for producing a cutting line, which runs as follows:

1) Command to the wedge plates of the deflecting unit 40 to move to the last already calculated angular position (α,β);
2) Calculation of the following shooting coordinates (x,y) on the basis of the current point spacing D;
3) Conversion of these shooting coordinates into angular positions (α,β) of the wedge plates of the deflecting unit 40 (the most time consuming, as a rule);
4) Waiting until all the components have reached their desired position, AND the selected period of the laser has expired;
5) Releasing a laser trigger and resetting the counter for the period;
6) Calculating the new values for the point spacing (dx, dy), the power P, therefrom values for aperture A and attenuator K, and, if appropriate, also the focal position F;
7) Command to aperture stop, attenuator and focus motor to move to the new position;
8) Back to 1) if the end point of the cutting curve has not yet been reached.

In order to start the sequence, the angular positions (α,β) of the first point of the cutting curve must already have been calculated once, and aperture A, attenuator K and focal position F must already be brought into the initial position for the starting point of the cutting curve.

In the case of the cutting method illustrated in FIG. 6, it is advantageous for the purpose of the invention to monitor the position of the last laser shot at the end of the cutting line and, if appropriate, to intervene correctively. During the laser microdissection with the highest laser power the last laser pulse should always be positioned directly, before the cutting curve closes, such that as large as possible a region of the dissectate is removed in order to ensure as reliable a detachment as possible. If the last shot is set too far removed from the starting point of the cutting line, there is the risk of the dissectate being left hanging, whereas if the last point is set too close by there is the risk of the dissectate not being severed as desired but (as often observed) "turning out" from the focal plane and thus also becoming "inaccessible" for the last shot.

However, the total lengths of the cutting curves, which are generally fixed arbitrarily by the user, are rarely an appropriate multiple of the point spacing, particularly when the point spacing does not remain constant in the expanded modes. The substance of the invention is therefore to calculate the position, resulting from the selected cutting parameters, of this last pulse before the beginning of the cutting operation and to compel an advantageous position of the last pulse by slight variations of the parameters without thereby giving rise to an interfering discontinuity or gaps in the cutting curve or cutting line.

Varying the laser power parameters (aperture and attenuator) synchronously with the laser pulses delivers an extremely high cutting speed. This gives rise to positive side effects that likewise maximize the throughput in conjunction with automatic cutting of many subregions.

By adapting the point density to the respective laser power and the local properties of the specimen, it can be ensured that the individual laser shots produce a cut. This prevents the dissectate from being left hanging, being tilted etc., or avoids the same. An optimization of the pulse transmission can also be achieved in conjunction with severance of the region of interest.

The simultaneous variation of aperture and attenuator attains as large a dynamic range as possible.

The combined driving of attenuator and aperture stop raises the resolution in the power setting.

Specific properties of the specimen (within the available dynamic range) can be taken into account optimally by the variation of effective laser power via aperture and attenuator using a specific scheme.

The "linearization" of the attenuator K is attained by an individual calibration curve stored in the laser head. The typically cos-shaped characteristic of a tilted interference filter is thereby converted into a correctly exponential profile.

Furthermore, the determination of the optimum parameters for the cutting process can be performed from an image analysis either in advance in a "calibration region" of the specimen or under current, automatic optical monitoring of the cutting results during cutting. If appropriate, it is also possible to automatically recut or cut anew regions of the specimen not optimally separated.

Figure 17:
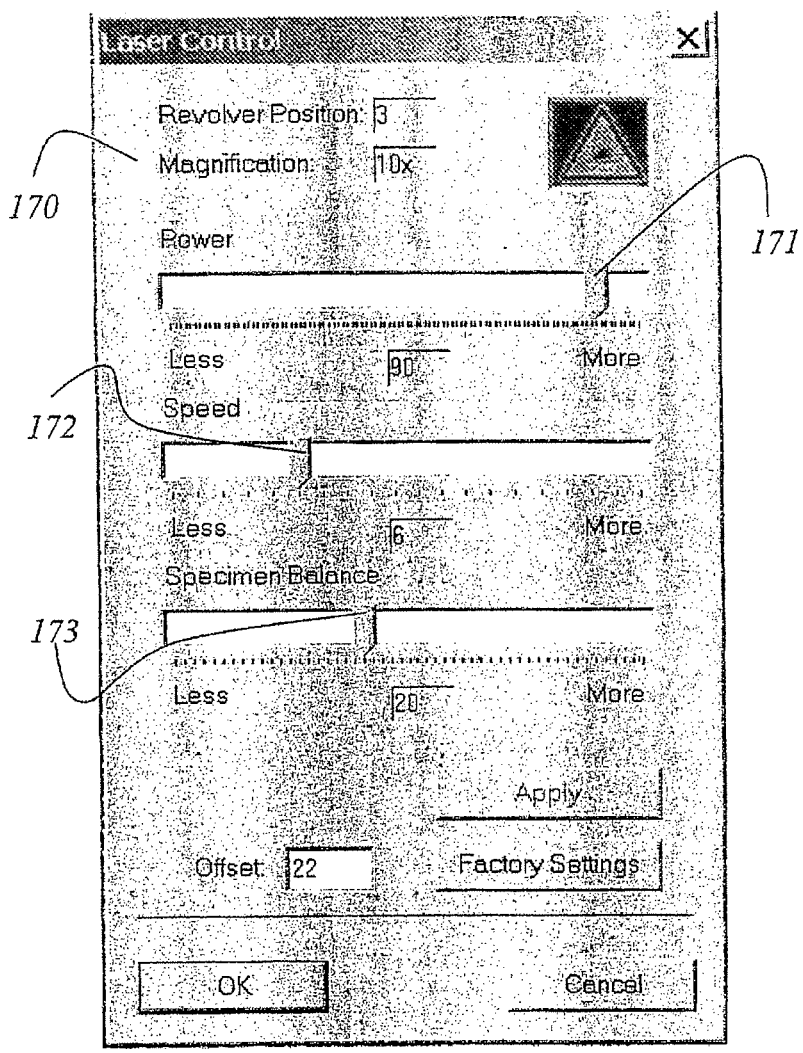
FIG. 17 shows a display of a section from a user interface via which the continuous variation of the parameters before the closure of the closed cutting line is set by means of a slider.

FIG. 17 shows an illustration of a section from a user interface 170 via which the continuous variation of the parameters before the closure of the closed cutting line is set by means of at least one slider 171, 172, 173. The user interface 170 is displayed to the user by the monitor 18. The first slider 171 can be used to set the total power of the laser pulses striking the specimen. As already described, the total power results from the suitable combination of the adjustment of attenuator and aperture. The second slider 172 can be used to set the speed with which the cutting lines are to be made in the specimen. The repetition rate of the laser pulses is then set in accordance therewith. The third slider 173 can be used to set how strongly the parameters are to be changed at the end of the cutting line.

The invention claimed is:

1. A laser microdissection method comprising:
mounting a biological specimen on a planar carrier;
cutting a dissectate as a desired part of the specimen along
a closed cutting line from the biological specimen by
laser pulses of a focused laser beam, wherein the laser pulses and the cutting line are determined by parameters; and
causing a series of cutting holes by relative movement of the focused laser beam to the specimen such that the laser beam describes the closed cutting line on the specimen in order to separate said dissectate from the rest of the surrounding biological specimen,
wherein at least one of the parameters that determine the laser pulses and the cutting line is continuously varied synchronously with the laser pulses along the closed cutting line, and
wherein the at least one of said parameters being varied comprises at least one of an aperture, an attenuation, a density of the individual laser points on the cutting line and a focal position of the laser pulses.

2. The method as claimed in claim 1, wherein the at least one of the parameters that determine the laser pulses and the cutting line is continuously varied only before a closure of the closed cutting line during the cutting of the dissectate.

3. The method as claimed in claim 2, wherein the at least one of the parameters that determine the laser pulses and the cutting line is continuously varied in at least one region of the cutting line comprising a plurality of laser pulses.

4. The method as claimed in claim 1, further comprising determining the at least one of the parameters by a central processor, wherein the central processor supplies control signals to individual elements of an optical system.

5. The method as claimed in claim 4, wherein the laser pulses traverse the optical system before striking the biological specimen, the at least one of the parameters being varied comprise the aperture, the attenuation, the density of individual laser points on the cutting line and the focal position of the laser pulses.

6. The method as claimed in claim 5, wherein the aperture and the attenuation are varied simultaneously.

7. The method as claimed in claim 5, wherein the variation of the aperture and the variation of the attenuation are performed synchronously with the laser pulses for highest cutting speed.

8. The method as claimed in claim 5, wherein the density of the individual laser points inside the cutting line is adapted with regard to respective laser power and local properties of the specimen.

9. The method as claimed in claim 5, wherein the aperture and the attenuation are continuously varied synchronously with the laser pulses.

10. The method as claimed in claim 1, wherein the at least one of the parameters that determine the laser pulses and the cutting line is continuously varied in at least one region of the cutting line comprising a plurality of laser pulses.

11. The method as claimed in claim 1, wherein the biological specimen is flat.

12. The method as claimed in claim 1, wherein the at least one of the parameters is varied according to variables which are dependent on the specimen.

13. The method as claimed in claim 12, further comprising obtaining the variables for the continuous variation of the at least one of the parameters along the closed cutting line by image processing.

14. The method as claimed in claim 13, wherein the variables comprise specimen thickness, oblique position of the carrier, specimen texture and specimen staining.

15. The method as claimed in claim 12, wherein the variables comprise specimen thickness, oblique position of the carrier, specimen texture and specimen staining.

16. A laser microdissection method comprising:
mounting a biological specimen on a planar carrier; and
cutting out a dissectate as a desired part of the specimen from the biological specimen by laser pulses of a focused laser beam by continuously varying parameters that determine the laser pulses and a closed cutting line with the laser pulses along the closed cutting line for a plurality of laser pulses covering at least a portion of the closed cutting line such that a series of cutting holes are formed by relative movement of the focused laser beam to the specimen,
wherein the laser pulses and the cutting line are determined by the parameters,
wherein at least one of the parameters that determine the laser pulses and the cutting lines is continuously varied synchronously with the laser pulses along the closed cutting line,
wherein the at least one of the parameters being varied comprises at least one of an aperture, an attenuation, a density of individual laser points on the cutting line and a focal position of the laser pulses.

17. The method as claimed in claim 16, wherein the at least one of the parameters being varied comprises the aperture, the attenuation, the density of individual laser points on the cutting line and the focal position of the laser pulses.

18. The method as claimed in claim 16, wherein the biological specimen is flat.

* * * * *